United States Patent [19]

Kirmann

[11] Patent Number: Plant 6,023

[45] Date of Patent: Sep. 22, 1987

[54] GERANIUM PLANT NAMED CANDY

[75] Inventor: Wolfgang Kirmann, Langenzersdorf, Austria

[73] Assignee: Mikro Vavra, Bisamberg, Austria

[21] Appl. No.: 810,705

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Candy having a floriferous habit, very compact and self-branching growth habit, light red-purple flower color with a much deeper red-purple variegation in the upper two petals, medium early flowering, good bud production at night temperatures up to 16° C., thus providing a long and continuous flowering period, and ease of propagation and good rooting habit.

2 Drawing Figures

The present invention comprises a new and distinct cultivar of geranium, botanically known as *Pelargonium domesticum,* and hereinafter referred to by the cultivar name Candy.

Candy is a product of a planned breeding program which had the objective of creating new geranium cultivars having compact growth habit, early flowering, long lasting flowers, good flower production, relatively small foliage, and red-purple flower color with deeper red-purple variegation.

Candy was originated from a hybridization made by applicant in a controlled breeding program in Bisamberg, Austria in 1978. The female parent was Morgengruss, a cultivar characterized by its compact, broad growth habit, light pink flower color with red eyes, and medium early flowering. The male parent of Candy was a cultivar designated as seedling 2/76, a vigorous, good flower producer having rose-pink flower color.

Candy was discovered and selected as one flowering plant within the progeny of the stated cross by applicant on Mar. 28, 1979 in a controlled environment in Bisamberg, Austria.

The first act of asexual reproduction of Candy was accomplished when vegetative cuttings were taken from the initial selection on Aug. 27, 1979 in a controlled environment in Bisamberg, Austria by a technician working under formulations established and supervised by Wolfgang Kirmann. Horticultural examination of selected units initiated in the spring of 1980 has demonstrated that the combination of characteristics as herein disclosed for Candy are firmly fixed and are retained through successive generations of asexual reproduction.

Candy has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Candy, which in combination distinguish this geranium as a new and distinct cultivar.

1. Propagates well, with very good rooting habit.
2. Excellent bud producer and very floriferous.

3. Medium early flowering, and long flowering period.
4. Very striking flower color, with main color being a light red-purple. Portions of certain petals are deeply variegated with a much darker and more intense red-purple color.
5. Medium green, stable foliage.
6. Very compact, self-branching growth habit, resulting in the setting of many buds.
7. Buds are produced under normal greenhouse conditions (5000 Lux for 16 hours per day) at 14°-16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
8. Candy is unique with regard to the combined features of compactness, continuous flowering, floriferous habit, and light red-purple flower color.

Of the many commercial cultivars known to the present inventor, the most similar in comparison to Candy is Quichita, an unpatented but commercial cultivar. In comparison to Quichita, Candy has a more compact growth habit, earlier flowering, larger flowers, more intense and striking color, and is more resistant to diseases and parasites.

The accompanying photographic drawings show typical flower and foliage characteristics of Candy, with colors being as true as possible with illustrations of this type.

Sheet 1 is a perspective view of a plotted plant of Candy.

Sheet 2 is a black and white print showing the upper surface of immature and mature plants of Candy.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.*—*Pelargonium domesticum.*

*Commercial.*—Commonly referred to as a "Martha Washington" geranium, and having the cultivar name Candy.

INFLORESCENCE

A. Umbel:

*Average diameter.*—Relatively large, 120–125 mm.

*Peduncle length.*—Normal.

*Pedicel length.*—Normal.

B. Corolla:

*Average diameter.*—50–70 mm; floriferousness results in total inflorescence extending beyond foliage.

*Form.*—5–7 petals, symmetric.

*Color (general tonality from a distance of three meters).*—Light red-purple, with deeper and more intense red-purple variegation on upper two petals.

*Color (upper surface).*—68C-D, upper two petals variegated with 60A, and an even more intensely variegated 59A in the throat.

C. Bud:

*Shape.*—Stocky, oval.

*Color.*—Light pink with red stripes.

D. Reproductive organs:

*Androecium.*—Reddish, 7–8 stamens.

Gynoecium.—Five to seven part.

E. Spring flowering response period: Medium early.

F. Durability: Very good.

PLANT

A. Foliage:

*Form.*—Zygomorphic with a nectar spur.

*Margin.*—Sharply crenate, with indentations.

*Color (upper surface).*—Medium green.

*Tolerance of Botrytis and soil fungi.*—Good.

B. General appearance and form:

*Internode length.*—Short.

*Branching pattern.*—Excellent.

*Height.*—Very compact.

I claim:

1. A new and distinct cultivar of geranium named Candy, as described and illustrated, and particularly characterized by its floriferous habit, very compact and self-branching growth habit, light red-purple flower color with a much deeper red-purple variegation in the upper two petals, medium early flowering, good bud production at night temperatures up to 16° C., thus providing a long and continuous flowering period, and by its ease of propagation and good rooting habit.

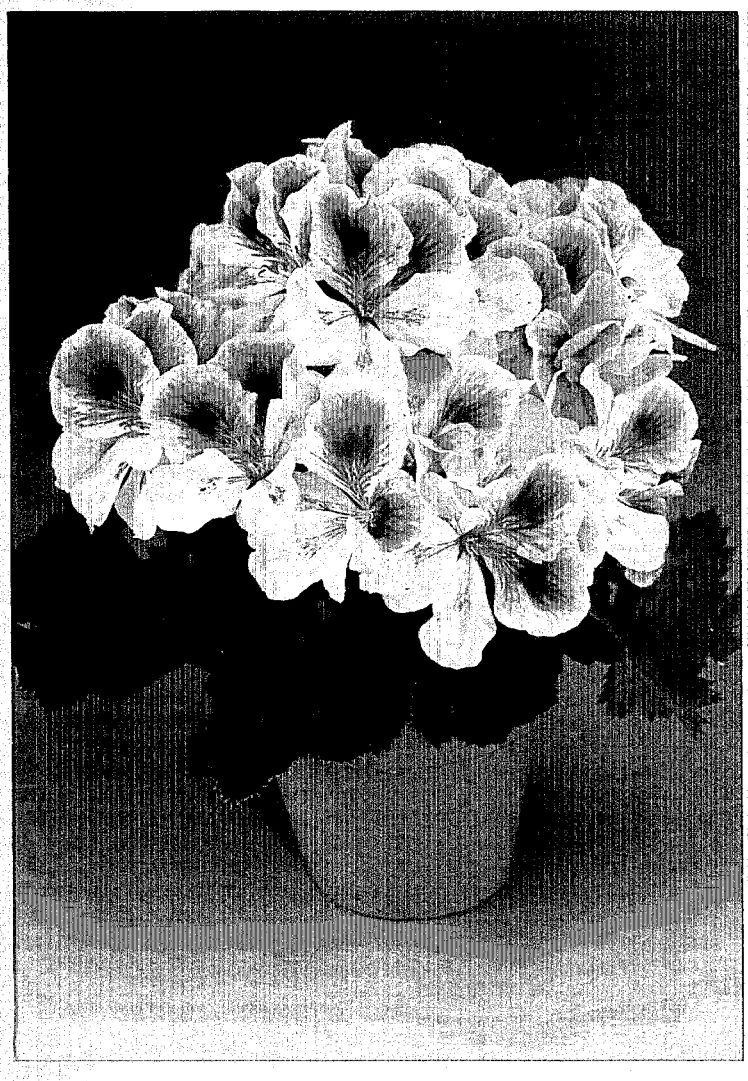

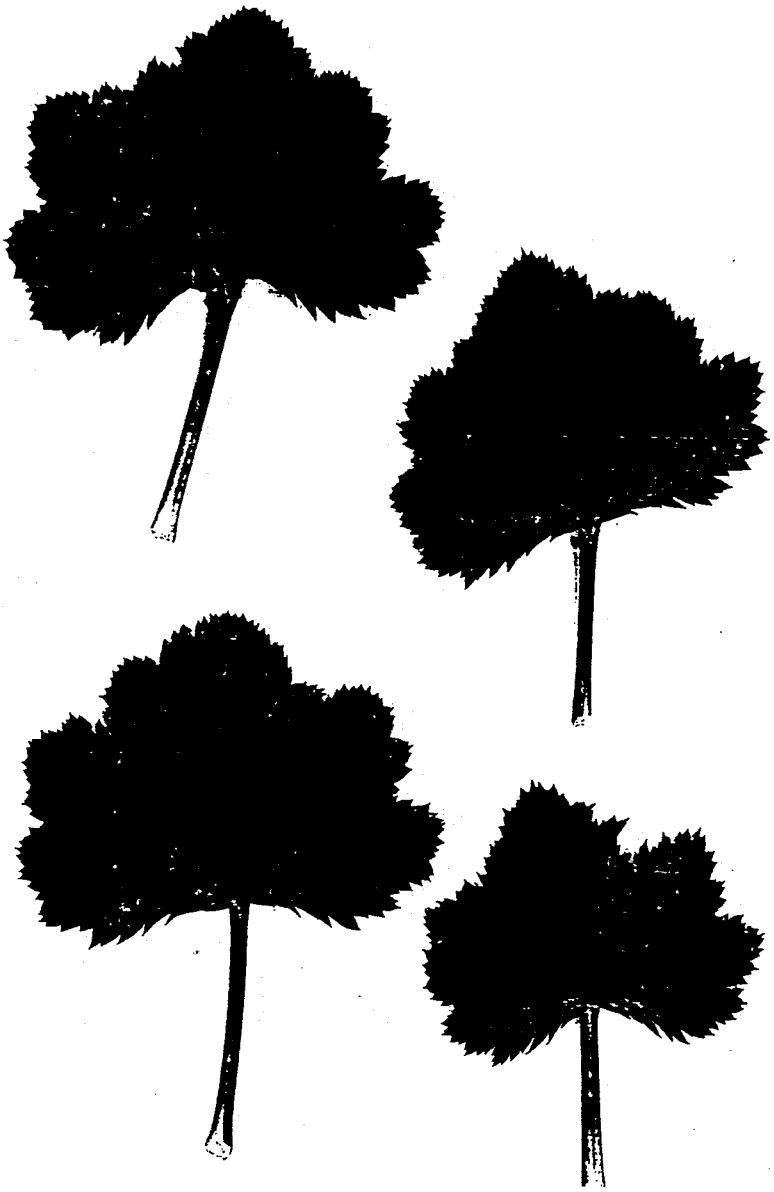

* * * * *